(12) United States Patent
Petrov et al.

(10) Patent No.: US 6,674,075 B2
(45) Date of Patent: Jan. 6, 2004

(54) CHARGED PARTICLE BEAM APPARATUS AND METHOD FOR INSPECTING SAMPLES

(75) Inventors: Igor Petrov, Holon (IL); Zvika Rosenberg, Jerusalem (IL)

(73) Assignee: Applied Materials, Inc., Santa Clara, CA (US)

( * ) Notice: Subject to any disclaimer, the term of this patent is extended or adjusted under 35 U.S.C. 154(b) by 11 days.

(21) Appl. No.: 10/146,218

(22) Filed: May 13, 2002

(65) Prior Publication Data

US 2003/0209667 A1 Nov. 13, 2003

(51) Int. Cl.[7] .............................. H01J 37/26; G21K 1/08
(52) U.S. Cl. ........................ 250/310; 250/307; 250/311; 250/396 R; 250/396 ML; 250/492.1
(58) Field of Search ................................. 250/305, 306, 250/309, 310, 307, 311, 396 R, 397, 492.1, 492.2, 492.3

(56) References Cited

U.S. PATENT DOCUMENTS

| | | | | |
|---|---|---|---|---|
| 4,896,036 A | * | 1/1990 | Rose et al. | 250/310 |
| 5,900,629 A | * | 5/1999 | Todokoro et al. | 250/310 |
| 5,939,720 A | * | 8/1999 | Todokoro | 250/310 |
| 6,066,853 A | * | 5/2000 | Nakasuji | 250/398 |
| 6,365,897 B1 | * | 4/2002 | Hamashima et al. | 250/310 |
| 2002/0185599 A1 | * | 12/2002 | Kimura et al. | 250/310 |

* cited by examiner

*Primary Examiner*—John R. Lee
*Assistant Examiner*—James P. Hughes
(74) *Attorney, Agent, or Firm*—Blakely Sokoloff Taylor & Zafman

(57) ABSTRACT

A beam directing method and device are presented for spatially separating between a primary charged particle beam and a beam of secondary particles returned from a sample as a result of its interaction with the primary charged particle beam. The primary charged particle beam is directed towards the beam directing device along a first axis passing an opening in a detector, which has charged particle detecting regions outside this opening. The trajectory of the primary charged particle beam is then affected to cause the primary charged particle beam propagation to the sample along a second axis substantially parallel to and spaced-apart from the first axis. This causes the secondary charged particle beam propagation to the detecting region outside the opening in the detector.

43 Claims, 7 Drawing Sheets

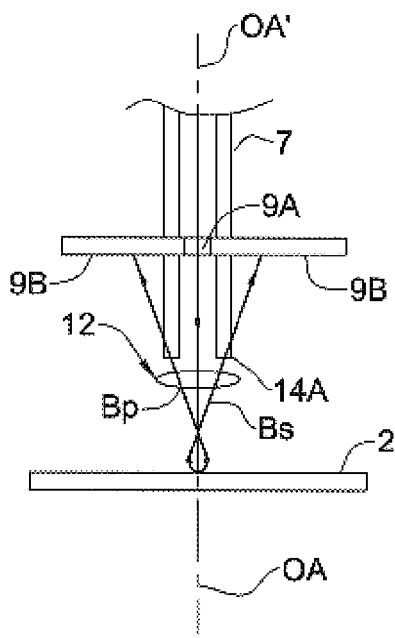 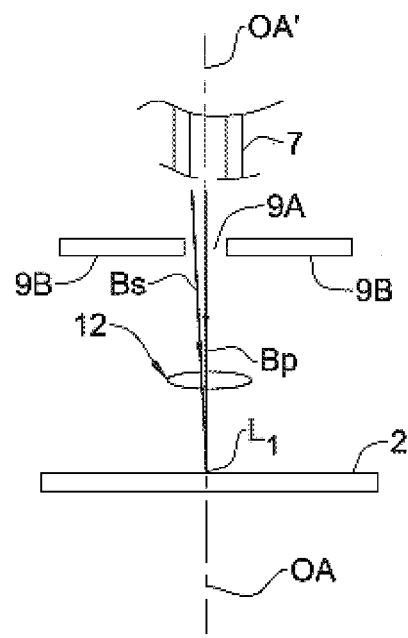
FIG. 2A  FIG. 2B
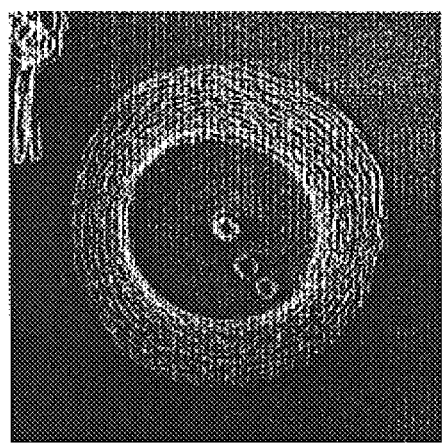 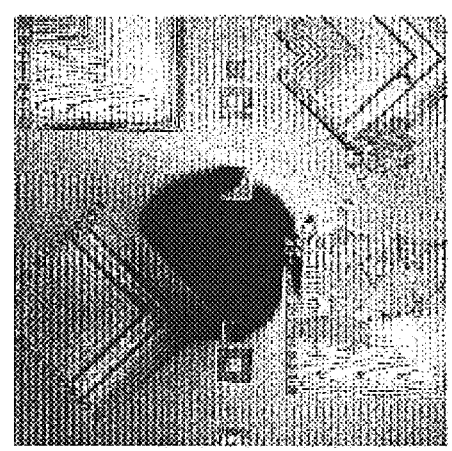
FIG. 3A  FIG. 3B

CHARGED PARTICLE BEAM APPARATUS AND METHOD FOR INSPECTING SAMPLES

FIELD OF THE INVENTION

The present invention relates to a beam directing device and a charged particle beam apparatus utilizing the same for inspecting samples by irradiating them with a focused beam of electrically charged particles, such as electrons, positrons, or ions. Such apparatus is used in the form of a scanning electron microscope (SEM), particularly for inspection of semiconductor wafers.

BACKGROUND OF THE INVENTION

Scanning electron microscopy is a known technique widely used in the manufacture of semiconductor wafers, being utilized in a Critical Dimension metrology tool, the so-called CD-SEM (critical dimension scanning electron microscope) and a defect review metrology tool SEM, the so-called DR-SEM (defect review scanning electron microscope). In a SEM, the surface region of a sample to be examined is two-dimensionally scanned by means of a primary beam of electrically charged particles, usually electrons, which travel along an optical axis of the apparatus. Irradiation of the sample with the primary electron beam releases secondary (or backscattered) electrons thereby defining a secondary electron beam. The secondary electrons are released at that side of the sample at which the primary electron beam is incident, and move back to be captured by a detector, which generates an output electric signal proportional to the so-detected secondary electron beam. The energy and/or the energy distribution of the secondary electrons is indicative of the nature and composition of the sample.

An SEM typically includes such main constructional parts as an electron beam source, an electron beam column, and a detection unit. The electron beam column comprises inter alia a beam aligning means (the so-called "alignment coils") and a beam shaping means (stigmator) arranged along an anode tube that defines a primary beam drift space, and comprises a focusing means for directing a primary electron beam onto a sample and directing secondary electrons towards one or more detection units. The focusing assembly typically includes an objective lens arrangement and scanning coils.

To increase the image resolution and improve image acquisition, the primary electron beam should be affected as little as possible, and secondary electrons should be completely detected. The increase of the image resolution can be achieved by reducing chromatic aberration of focusing and deflection. WO 01/45136 assigned to the assignee of the present application discloses a deflection and focusing technique, wherein chromatic aberrations are compensated by using one or two deflections of the primary electron beam propagating towards the sample, i.e., the pre-lens deflection, in-lens deflection, or both. The complete detection of the secondary electrons requires spatial separation between the primary and secondary electrons and the effective detection of the secondary electrons (with minimal losses of electrons).

In many cases, the detector is accommodated above the objective lens outside the path of the primary beam propagation through the column. To direct secondary electrons to the detector, a generator of orthogonal electric and magnetic fields (known as Wien-filter) is used (e.g., U.S. Pat. Nos. 5,894,124; 5,900,629). To ensure detection of those secondary electrons that are not sufficiently deflected by the Wien-filter, a target or extracting electrode made of a material capable of generating a secondary electron when an electron collides therewith is additionally used. Such a target is formed with an aperture and is located such that the axis of the primary beam propagation towards the focusing means intersects with this aperture, which thereby serves as a primary beam hole.

To eliminate the use of the Wien-filter, which requires extensive care and is difficult to adjust, WO 99/26272 suggests scanning a sample with one or more angles of incidence of the primary beam. According to this technique, the primary beam is directed to run diagonally to the optical axis of the focusing assembly, and is redirected into the optical axis by a redirection unit arranged below the plane of a detector accommodated outside the primary beam path. The redirection unit also affects secondary electrons in the sense that it separates primary and secondary electrons.

The technique of the above-indicated publication WO 01/45136, assigned to the assignee of the present application, utilizes a secondary electrons' detector formed with a primary beam hole that is located in the path of a primary electron beam propagating towards the focusing assembly. Here, a deflection system is located downstream of the detector (with respect to the direction of the primary electron beam propagation towards the sample) and operates to affect the trajectory of the primary electron beam such that the primary electron beam impinges onto a sample along an axis forming a certain angle with the sample's surface (the so-called "tilt mode"). This is aimed at solving another problem of the inspection systems of the kind specified associated with inspecting and/or measuring on patterned surfaces. The pattern is typically in the form of a plurality of spaced-apart grooves. To detect the existence of a foreign particle located inside a narrow groove, it is desirable to tilt the scanning beam with respect to the surface. Generally, a tilt mechanism can be implemented by mechanically tilting either the sample carrier relative to the charged particle beam column (e.g., U.S. Pat. Nos. 5,734,164; 5,894,124; 6,037,589) or the column (e.g., U.S. Pat. No. 5,329,125). The technique of WO 01/45136 achieves a tilt mechanism by affecting the trajectory of the primary electron beam using single- or double-deflection. However, the column's configuration of WO 01/45136 while providing effective detection of secondary electrons with the above-described tilt mode of operation, will be problematic for detecting secondary electrons, especially fast electrons (the so-called HAR mode), when operating with normal incidence of the primary beam, i.e., beam incidence substantially perpendicular to the sample's surface.

SUMMARY OF THE INVENTION

There is accordingly a need in the art to improve inspection of samples with a charged particle beam by providing a novel beam directing method and device, and a charged particle beam apparatus utilizing the same.

The main idea of the present invention consists of providing effective detection of a secondary charged particle beam with a detector, which is made with an opening and has detecting regions outside this opening, and which is accommodated in the path of the primary charged particle beam such that the primary beam propagation axis intersects with the opening, which therefore serves as a primary beam hole. This is the so-called "in-column detector". The present invention provides for affecting the trajectories of primary and secondary charged particle beams propagating through a beam directing device to cause a desired incidence of the primary charged particle beam onto a sample, and to cause propagation of the secondary beam to a region of the detector outside the primary beam hole.

The term "primary beam" or "primary charged particle beam" used herein signifies a charged particle beam, which is formed by charged particles generated by a source (cathode), and which is to be directed to a sample to knock out charged particles forming a "secondary beam" (also referred to as "secondary charged particle beam", which is to be detected.

The above is implemented by deflecting the primary beam entering the beam directing device along a first axis of beam propagation, so as to cause the primary beam incidence onto the sample along a second axis that is spaced-apart from the first axis, thereby causing the secondary beam propagation towards a region of the detector outside the primary beam hole.

The present invention enables operation in both the "normal" and "tilt" operational modes without the need for inclining the sample with respect to the charged particle beam apparatus or vice versa. The term "normal mode" used herein signifies the primary beam incidence onto the sample with substantially zero incident angle, i.e., substantially perpendicular to the sample's surface. The term "tilt mode" used herein signifies the primary beam incidence onto the sample along an axis forming a certain non-zero angle with the sample's surface.

Thus, according to one aspect of the present invention, there is provided a method of separating between a primary charged particle beam and a secondary charged particle beam, the secondary charged particle beam resulting from interaction of the primary charged particle beam with the sample, the method comprising:

(a) directing the primary charged particle beam along a first axis passing through an opening in a detector, which has charged particle detecting regions outside said opening;

(b) affecting the trajectory of the primary charged particle beam to provide the primary charged particle beam propagation to the sample along a second axis substantially parallel to and spaced apart from said first axis, thereby causing the secondary charged particle beam propagation to the detecting region of said detector outside said opening.

The present invention, according to its another broad aspect, provides a method of inspecting a sample with a charged particle beam, utilizing the above technique of separating the primary and secondary charged particle beams.

The arrangement is preferably such that the first axis (typically defined by the longitudinal axis of the anode tube) is substantially perpendicular to the sample's surface. The present invention also provides for operating with a column of the kind having an anode tube (defining the first axis) inclined with respect to the sample's plane. In this case, the trajectory of the primary charged particle beam is affected to provide the primary charged particle beam propagation along the second axis, which forms an angle with said first axis.

There is thus provided according to yet another aspect of the invention, a method of separating between a primary charged particle beam and a secondary charged particle beam, the secondary charged particle beam resulting from interaction of the primary charged particle beam with the sample, the method comprising:

directing the primary charged particle beam towards a beam directing device along a first axis passing through an opening in a detector, which has charged particle detecting regions outside said opening;

passing the primary charged particle beam through the beam directing device that includes a focusing assembly defining an optical axis forming an angle with said first axis, and a deflection assembly, the deflection assembly being operable to deflect the primary charged particle beam from its propagation along the first axis to the propagation of the primary charged particle beam to the sample along a second axis substantially parallel to the optical axis of the focusing assembly, and to affect the trajectory of the secondary charged particle beam to provide the secondary charged particle beam propagation to the detecting region of said detector outside said opening.

Generally speaking, the second axis of the primary charged particle beam incidence onto the sample intersects the sample at a location spaced apart from a location of intersection between the first axis and the sample.

The beam directing device comprises a focusing assembly (including an objective lens arrangement) that defines an optical axis, and a deflection assembly operable to produce deflection fields that affect the trajectory of each of the primary and secondary beams with respect to the optical axis of the focusing assembly.

In the preferred embodiment of the invention, the first axis of the primary beam propagation towards the beam directing device is substantially parallel to the optical axis of the focusing assembly. This can be implemented by directing the primary beam towards the beam directing device either along the first axis coinciding with the optical axis of the focusing assembly or along the first axis spaced-apart from the optical axis of the focusing assembly. In this case, at least two deflection fields are used to separate between the paths of the primary and secondary beams and ensure the secondary beam propagation to the regions of the detector outside the primary beam hole. The two deflection fields may be pre-lens, pre-lens and in-lens, or in-lens and post-lens (with respect to the deflectors location relative to the objective lens). To eliminate or at least significantly reduce chromatic aberrations of focusing and deflection, either the same two deflection fields, or one or two additional deflection fields can be used.

In another embodiment of the invention, the first axis of the primary beam propagation towards the beam directing device is inclined with respect to the optical axis of the focusing assembly. In this case, the provision of the single deflection field within the beam directing device is sufficient for successful separation between the paths of the primary and secondary beams (i.e., prevent the secondary beam from passing through the primary beam hole of the detector.

It may be desired to incident the primary beam onto the sample with a certain non-zero incident angle (tilt mode). Moreover, the case may be such that the tilt mode is to be applied selectively, namely, to selective locations of the sample, while enabling inspection of this and other locations with the normal mode. To enable application of the tilt mode, the trajectory of the primary beam, as well as that of the secondary beam, is appropriately affected by at least two deflection fields.

There is thus provided, according to yet another broad aspect of the present invention, a beam directing device for use in a charged particle beam apparatus, which defines a primary charged particle beam propagating towards the beam directing device along a first axis and utilizes a detector that is formed with an opening and charged particle detecting regions outside said opening and is accommodated such that said first axis passes through said opening of the detector, the beam directing device comprising:

a focusing assembly that defines an optical axis and is operable to focus the primary charged particle beam onto a sample; and a deflection assembly operable to affect the trajectory of the primary charged particle beam to direct the primary charged particle beam onto the sample along a second axis substantially parallel to and spaced-apart from said first axis, thereby causing the secondary charged particle beam propagation to the detecting region of said detector outside said opening.

There is also provided according to the invention, a charged particle beam apparatus for inspecting a sample comprising:

an anode tube defining a space of propagation of a primary beam of charged particles, generated by a particles' source, along a first axis substantially parallel to a longitudinal axis of the anode tube;

a detector formed with an opening and having charged particle detecting regions outside said opening, the detector being accommodated such that said first axis intersects with said opening; and a beam directing device accommodated in the path of the primary charged particle beam passed through said opening in the detector, the beam directing device comprising a focusing assembly, which defines an optical axis and is operable to focus the primary charged particle beam onto the sample, and a deflection assembly, which is operable to affect the trajectory of the primary charged particle beam to direct the primary charged particle beam onto the sample along a second axis substantially parallel to and spaced-apart from said first axis, and to affect the trajectory of the secondary charged particle beam, thereby providing the secondary charged particle beam propagation to the region of said detector outside said opening.

According a preferred embodiment of the invention, the beam directing device is accommodated such that the optical axis of the focusing assembly is parallel to the longitudinal axis of the anode tube. The deflection assembly comprises at least two deflectors accommodated and operated to sequentially affect the trajectory of the primary charged particle beam at successive regions along the optical axis, and consequently sequentially affect the trajectory of the secondary charged particle beam.

The above can be implemented by substantially coinciding the optical axis of the focusing assembly with the longitudinal axis of the anode tube. In other words, the primary beam enters the beam directing device substantially along the optical axis of the focusing assembly. With this situation, in the normal mode, the primary beam hits the sample at a location spaced-apart from the location of intersection between the optical axis and the sample's surface. As for the tilt mode, the primary beam impinges onto the sample with a certain angle of incidence so as to hit the sample either at the location in which the optical axis intersects the sample or at the location of the primary beam incidence with the normal mode. Alternatively, the optical axis of the focusing assembly can be spaced-apart from the longitudinal axis of the anode tube. This enables to provide the normal incidence of the primary beam onto the sample substantially along the optical axis and the focusing assembly.

According to another embodiment of the apparatus, the longitudinal axis of the anode tube (defining the first axis) is inclined with respect to the optical axis of the focusing assembly. In this case, the deflection assembly is operable to provide the primary charged particle beam propagation to the sample along the second axis substantially coinciding with the optical axis of the focusing assembly.

The charged particle beam may be an electron beam or a focused ion beam (FIB). The present invention may be used in an SEM or the like tool applied to a specimen, e.g., a semiconductor wafer, for imaging, measurements, metrology, inspection, defect review or the like purposes. For example, the present invention may be used for CD measurements, line profile measurements, copper-interconnects inspection/measurements typically performed after a photolithography process, automatic defect classification, etc.

More specifically, the present invention is used with a SEM system for inspecting wafers, masks or reticles, and is therefore described below with respect to this application.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 2A and 2B schematically illustrate the primary and secondary beam propagation through the conventional beam directing device at different working parameters of the device, showing the problem to be solved by the beam directing device of the present invention;

FIGS. 3A and 3B illustrate images of the sample obtained with the situations of FIGS. 2A and 2B, respectively;

DETAILED DESCRIPTION OF A PREFERRED EMBODIMENT

Figure 1:
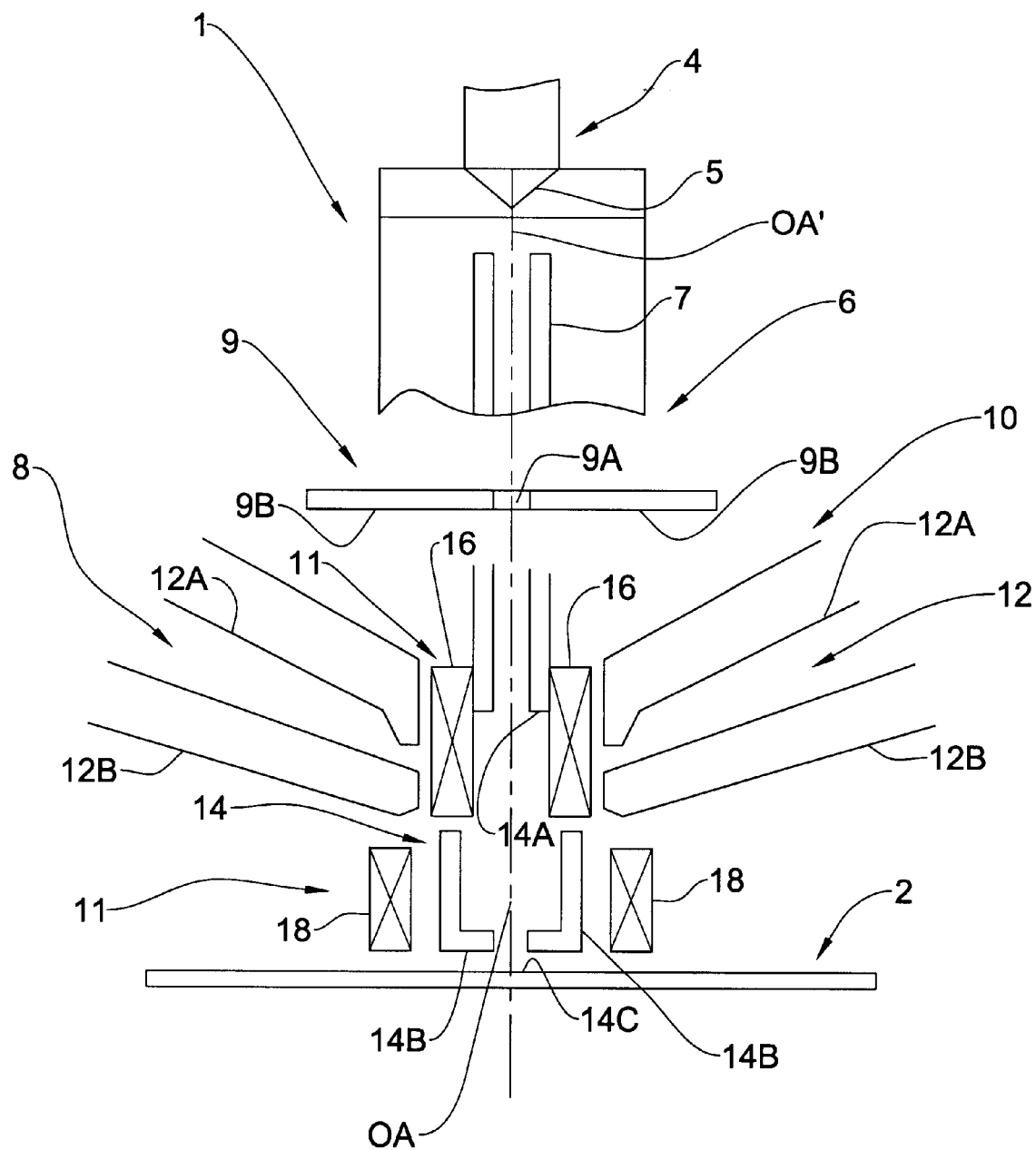
FIG. 1 is a schematic illustration of an SEM system utilizing a charged particle beam apparatus according to one embodiment of the invention.

Referring to FIG. 1, there are illustrated the main components of an SEM system, generally designated 1, associated with a wafer 2 to be inspected. The system 1 typically comprises an electron beam source 4 having a small tip 5 (a so-called "electron gun"), and a charged particle beam apparatus 6. The apparatus 6 comprises an anode tube 7 defining a primary beam drift space, a beam directing device 8, and a detector 9, which is located upstream of the beam directing device 8 (with respect to the direction of primary beam propagation towards the wafer 2). The apparatus 6 also typically comprises beam blank means, several apertures (including a final aperture defining the primary beam diameter, and alignment coils), and a stigmator arrangement.

These elements do not form part of the present invention, their construction and operation are known per se, and they therefore need not be specifically described.

The longitudinal axis of the anode tube 7 defines a first axis OA' of the primary beam propagation (not shown here) towards the beam directing device 8. The detector 9 is shaped like a plate (or disc) formed with a central opening 9A and having detecting regions 9B outside the opening 9A. The detector 9 is the so-called "in-column detector" located such that the longitudinal axis of the anode tube 7 passes the central opening, which thus serves as a primary beam hole 9a. The beam directing device 8 is composed of a focusing assembly 10 and a deflection assembly 11. Additional scanning coils (not shown) for two-dimensional scanning of the wafer with the primary beam may be provided in the vicinity of the focusing assembly in the conventional manner.

In the present example, the beam directing device 8 utilizes the focusing assembly disclosed in the co-pending U.S. application Ser. No. 09/479,664 assigned to the assignee of the present application. It should however be understood that any other suitable design of the focusing assembly can be used.

Thus, in the present example, the focusing assembly 10 is composed of an objective lens 12, which is typically a magnetic lens formed by two pole pieces 12a and 12b, and a retarding electrostatic immersion lens 14 formed by several electrodes—three electrodes 14a, 14b and 14c. The lower end of the anode tube 7 serves as the first electrode 14a, the wafer's surface serves as the second electrode 14c, and the third electrode 14b is located between the electrodes 14a and 14c, and serves for regulating an electric field created within the vicinity of the wafer. Any other suitable design of the electrostatic immersion lens is possible. The lenses 12 and 14 present together an objective lens arrangement and define an optical axis OA of the focusing assembly 10. In the present example, the axes OA' and OA substantially coincide.

The electrostatic lens 14 acts to decelerate the electrons in the closest vicinity of the wafer 2. This is associated with the following: In an SEM, in order to reduce the "spot" size of the primary electron beam up to nanometers (i.e., to increase image resolution), a highly accelerated primary electron beam is typically produced using accelerating voltages of several tens of kilovolts and more. However, in order to prevent damaging resist structures and integrated circuits, and, in the case of dialectical specimens, prevent undesirable charging of the specimen with such a high-energy primary beam, a retarding field is provided in the path of a deflected focused primary beam, thereby reducing the aberration of focusing and deflection. The landing energy of the primary electron beam is defined by the potential difference between the cathode and the sample. To achieve the desired acceleration of electrons, appropriate potential difference between the cathode 5 and anode 7 should be provided. For example, the cathode voltage can be about (−1)kV and the anode voltage can be about (+8)kV. Hence, the electrons are accelerated on their way towards the magnetic lens 12 having the velocities of 9 keV. To create the retarding filed, the voltage applied to the second electrode 14c (wafer's surface) of the electrostatic lens 14 is typically substantially less than that of the anode 7. For example, the case may be such that the wafer is grounded ($V_2=0$), and the electrodes are biased, that is the following voltages may be applied to, respectively, cathode 5, anode 7 and third electrode 14b:(−1)kV; (+8)kV and (+3)kV It should be noted that the provision of any electrostatic lens as an actual physical element is optional. The same effect of electrons' deceleration, namely the creation of a retarding electric field, may be achieved by applying appropriate voltages to the anode and wafer, or to anode, pole piece and wafer. The following are two possible examples of the electric parameters:

(1) the wafer is biased to (−5)kV, the anode voltage is equal to zero and the cathode voltage is (−6)kV;

(2) the wafer is biased to (−3)kV, the pole piece voltage is equal to zero, and the anode and cathode voltage are, respectively, (+5)kV and (−4)kV The decelerated primary electron beam impinges onto the wafer's surface within a scan area, and knocks-out secondary electrons. The electric field produced, for example, by the electrostatic lens 14, whilst decelerating the primary electrons, acts as an accelerating field for the secondary electrons, and thereby provides the propagation of the secondary electrons away from the sample's surface (towards the detector).

The deflection assembly 11 is composed of two deflectors 16 and 18, which in the present example are, respectively, the so-called in-lens and post-lens deflectors with respect to the direction of the primary beam propagation towards the wafer. It should be understood that these terms correspond to the deflectors' locations relative to the pole pieces of the objective lens 12, while both deflectors being located within the focusing field of the entire lens arrangement 10. The first deflector 16 is mounted within the magnetic lens gap (i.e., between the pole pieces 12A and 12B), and the second deflector 18 is mounted within the electrostatic field produced by the lens 14. The second deflector 18 may be either magnetic (as in the present example), or electrostatic, e.g., in the form of condenser plates. The deflectors 16 and 18 operate together to provide incidence of the primary beam onto the sample along a second axis and provide the secondary beam propagation to a detector area within the regions 9b outside the primary beam hole 9a, as will be described more specifically further below. It should be noted that the same or additional deflectors can be used for scanning purposes.

Reference is now made to FIGS. 2A–2B and 3A–3B illustrating a problem to be solved by the present invention, namely, providing effective detection of a secondary electron beam produced by the interaction between a primary electron beam and a sample, with the "in-column detector". As indicated above, to achieve this, the secondary beam should be directed to the detector area within the regions 9b outside the primary beam hole 9a, to thereby prevent secondary electron losses in the primary beam hole.

In the examples of FIGS. 2A and 2B, no deflection fields are provided in the primary beam path through the beam directing device. The primary electron beam $B_p$ propagates through the anode tube 7 along the first axis OA' (substantially along the longitudinal axis of the anode tube 7), passes through the opening 9a (primary beam hole) of the detector 9, and then impinges onto the wafer 2 along the optical axis OA of the focusing assembly substantially coinciding with the first axis OA'. In both examples, the lower end of the anode tube 7 (electrode 14A of the electrostatic lens shown in FIG. 1) is maintained at voltage $V_{anode}$ equal to 8 kV.

In the example of FIG. 2A, no voltage is supplied to the cup-electrode of the electrostatic lens (14B in FIG. 1), i.e., $V_{cup}=0V$. In this case, an electric field created in the vicinity of the wafer by the electrostatic lens is a low gradient field. The electrostatic lens thus acts as a short-focus lens for the secondary electrons $B_s$. As a result, the secondary electrons $B_s$ cross over the optical axis OA in the vicinity of the wafer 2, and become directed to the regions 9b of the detector 9 at opposite sides of the primary beam hole 9a. FIG. 3A illustrates an image acquired with this operational condition ($V_{cup}=0V$, normal incidence) and with the field of view or raster size of 2 μm. As shown, the entire wafer's region irradiated with the primary electrons can be observed.

FIGS. 2B and 3B show the situation with the normal incidence of the primary beam $B_p$, and the high aspect ratio (HAR) mode, which is typically the case and can be achieved in the construction of FIG. 1 by applying $V_{cup}$ of about 3 kV to the electrode 14B. In this case, the electric field in the vicinity of the wafer is a high gradient field, and therefore the secondary electrons B, propagate from a location $L_1$ of the primary beam interaction with the wafer substantially along the optical axis OA, and are lost in the primary beam hole 9a. As a result, a black spot covers the central area of the imaged region of the wafer (raster).

Figure 4:
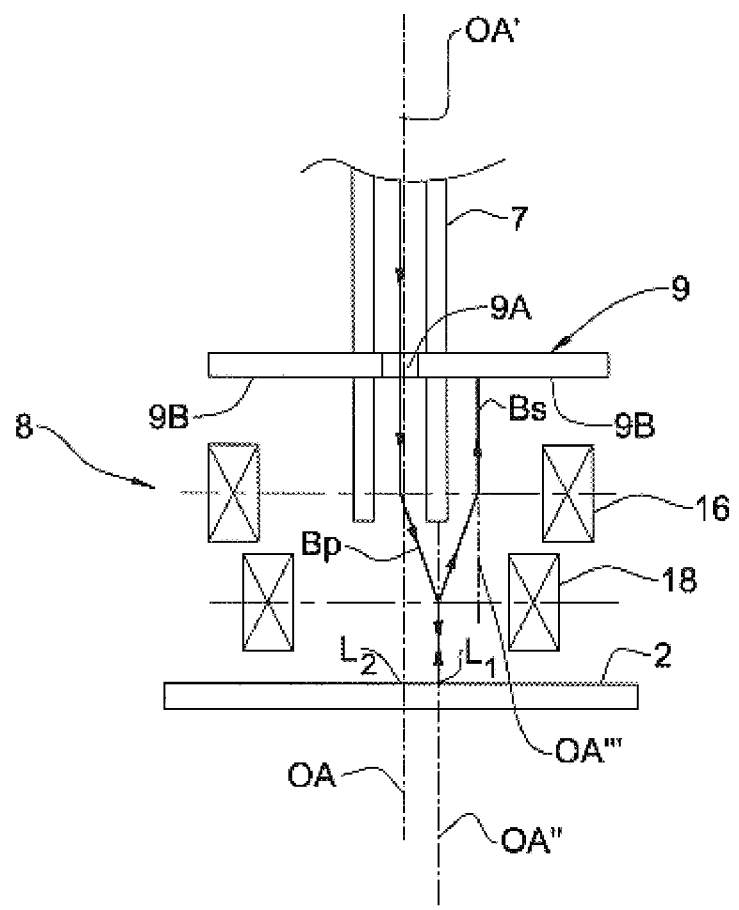
FIG. 4 illustrates the primary and secondary beam propagation in the beam directing device of the present invention.

Turning now to FIG. 4, the beams' propagation through the beam directing device 8 of FIG. 1 operating with the HAR mode (Vcup=3 kV) is schematically illustrated. The primary beam $B_p$ propagates through the anode tube 7 along the first axis OA', passes through the primary beam hole 9a of the detector 9, and enters the beam directing device 8. In the preferred embodiment of the invention, the first axis OA" is generally parallel to the optical axis OA of the focusing assembly, and in the present example, substantially coincides with the optical axis. In the beam directing device, the primary beam $B_p$ is deflected by the first deflection field of the first deflector in a direction away from the optical axis OA (forming an angle of few degrees, preferably 1–3 degrees, with the optical axis), and is then deflected by the second deflection field of the second deflector 18 to propagate along a second axis OA", which is parallel to and spaced-apart from the first axis of the primary beam propagation OA'. The second axis OA" intersects the wafer's surface at a location L1 spaced-apart (e.g., a distance of about 50–100 μm) from a location $L_2$ of intersection between the wafer's surface and the first axis OA'.

The secondary beam $B_s$ propagates back from the location $L_1$ along the axis OA" (generally, along an axis parallel to the optical axis of the focusing assembly) until it enters the deflection field of the second deflector 18, which deflects the beam $B_s$ away from the axis OA". The deflection field of the first deflector 16 then deflects the secondary beam $B_s$ in an opposite direction (as compared to that of the first deflection field), thereby ensuring the secondary beam propagation along an axis OA''' to the region 9b of the detector. In the present example, the axis OA''' is parallel to the optical axis OA (as well as to the first axis OA'). It should, however, be understood that this is not a necessary condition.

Figure 5A:
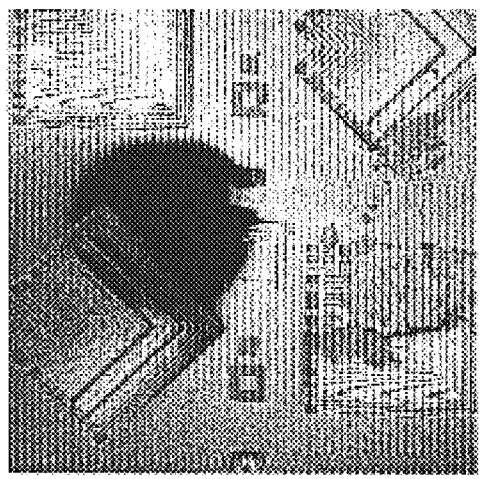
FIGS. 5A and 5B illustrates images of the sample obtained the beam directing device of the invention.
Figure 5B:
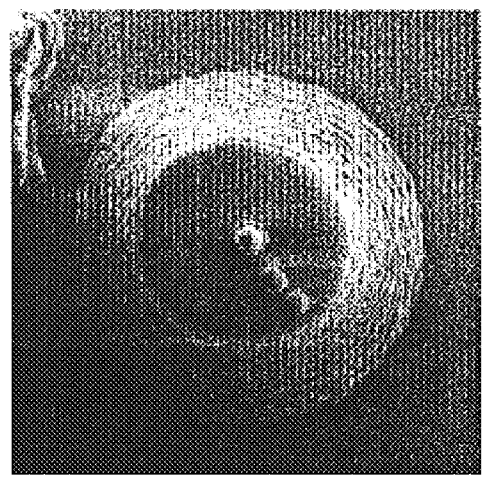

FIGS. 5A and 5B illustrate the experimental results obtained with the above situation of FIG. 4, wherein electric currents of 0.05A and 0.07A are supplied to the deflectors 16 and 18, and the primary beam hole 9a is of a 1 mm diameter. In these two experiments, the values of FOV are, respectively, 820 μm and 2 μm. As shown, even with a higher FOV value (FIG. 5A), the black spot (primary beam hole) is shifted aside from the central area of the irradiated region, and by reducing the FOV value (FIG. 5B), the entire irradiated region can be seen.

Figure 6:
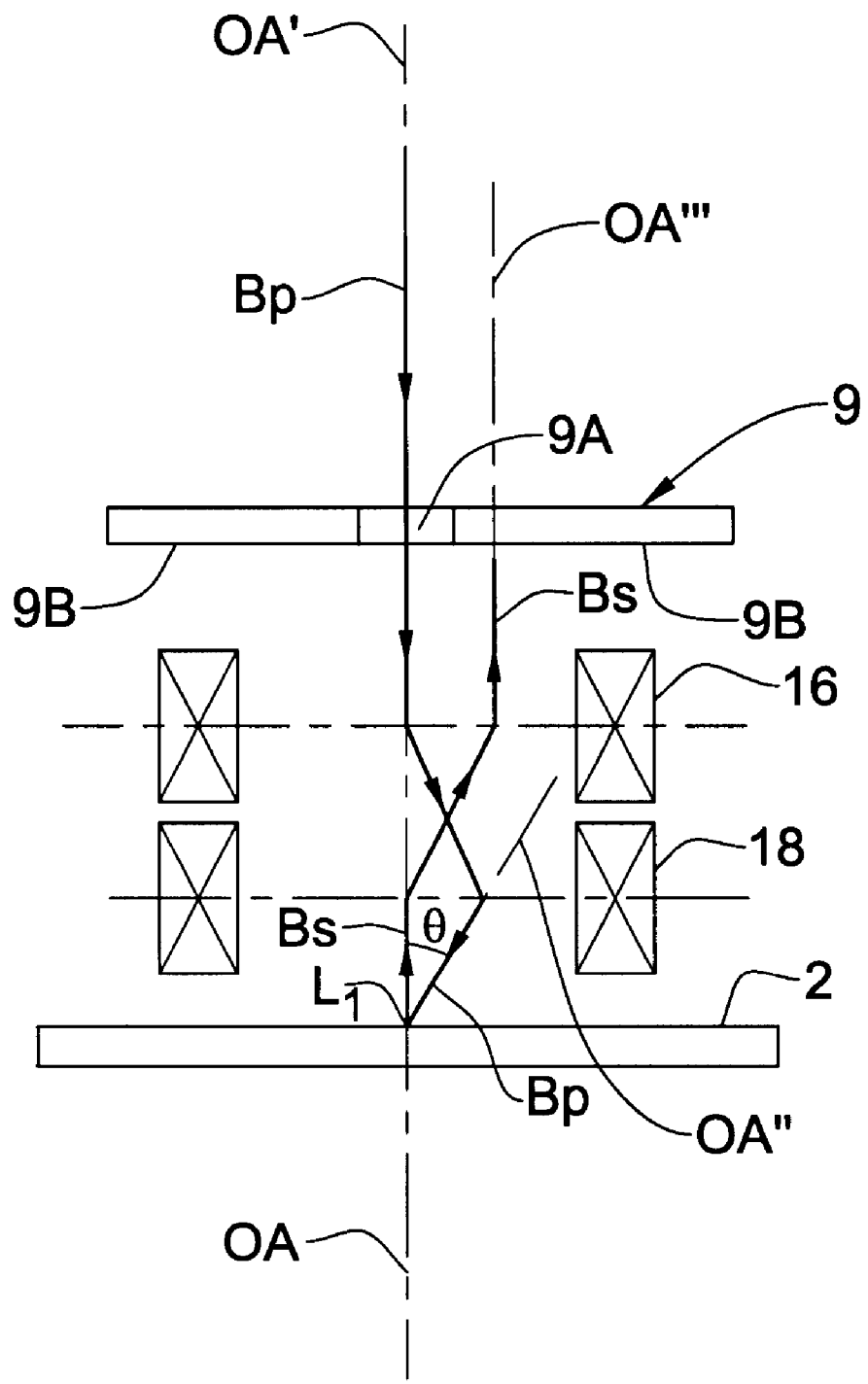
FIG. 6 schematically illustrates the tilt mode of operation of the beam directing device of the invention.

FIG. 6 illustrates the tilt mode of operation of the beam directing device 8 of FIG. 1. This is achieved by increasing electric currents through the deflectors 16 and 18 (as compared to those used in the normal mode), to be, for example, 0.7A and 0.6A respectively. As shown, the primary beam $B_p$ is sequentially affected by the deflection fields of the deflectors 16 and 18, resulting in the primary beam incidence onto the location $L_1$ on the wafer 2 along an axis OA" forming a certain angle θ (e.g., 15°-angle) with the optical axis OA. The secondary beam $B_s$ initially propagate from the location $L_1$ along an axis parallel to the optical axis OA of the focusing assembly, and is then sequentially deflected by the deflectors 18 and 16 to propagate along an axis OA''' towards the region 9b of the detector.

As indicated above, the tilt mode allows for inspecting patterned surfaces (i.e., formed with a plurality of grooves) to enable the so-called "side wall imaging" to detect foreign particles located on the groove's wall, and/or measure the groove's dimensions. Even a small angle of incidence (3°–60) of the primary beam onto the wafer's surface is sufficient for these purposes. In most cases, it would be desirable to apply this "tilt" mode selectively. This means that whilst the successive areas of the wafer are continuously inspected with the normal mode, at a specific location (i.e., for a specific area) the system should be switched to the "tilt" mode.

Figure 7C:
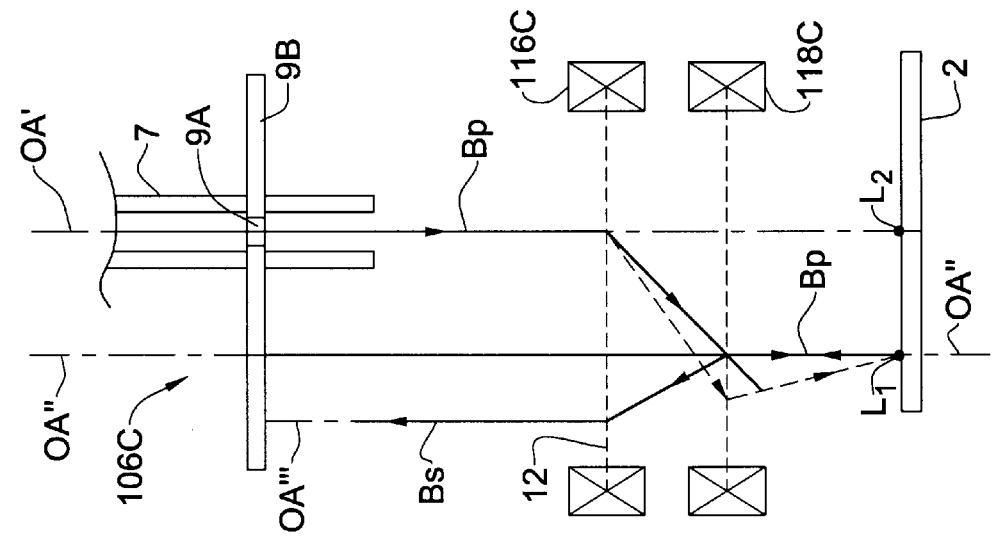
FIGS. 7A to 7C illustrate three different examples, respectively, of a charged particle beam apparatus according to another embodiment of the invention.
Figure 7B:
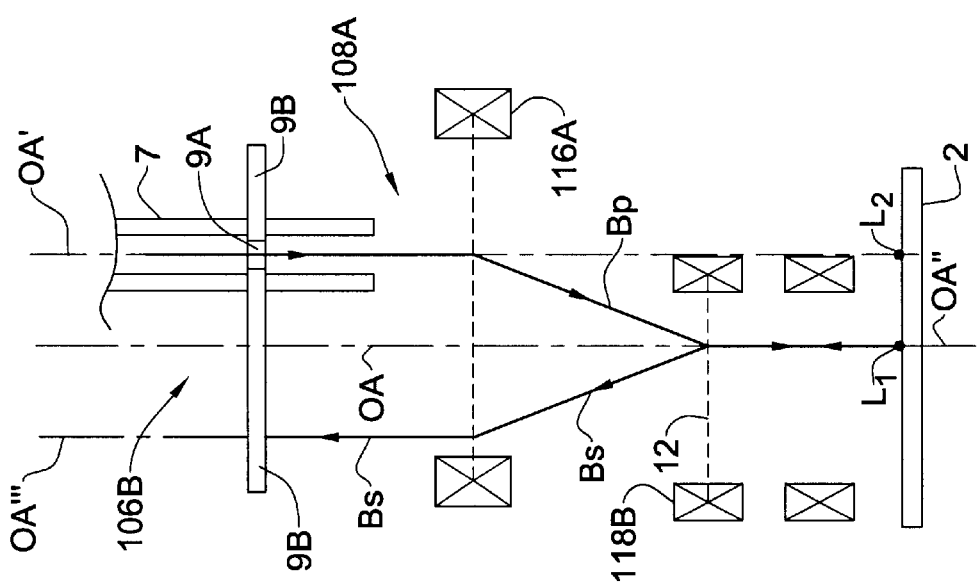
Figure 7A:
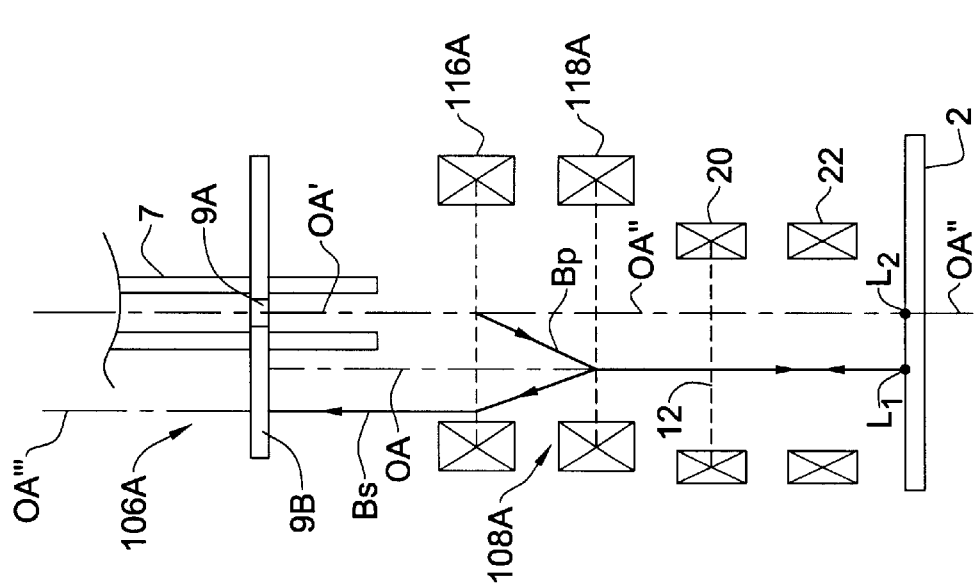

Referring to FIGS. 7A–7C, three examples, respectively, of another embodiment of the invention are illustrated. To facilitate understating, the same reference numbers are used for identifying those components which are identical in the charged particle beam apparatus 1 of FIG. 1 and apparatuses 106A, 106B and 106C of FIGS. 7A–7C. In these examples, in distinction to the example of FIG. 1, the longitudinal axis OA' of the anode tube 7 (i.e., the first axis of the primary beam propagation towards the beam directing device 8) and the optical axis OA of the focusing assembly are aligned in a spaced-apart parallel relationship intersecting the wafer's surface at locations $L_2$ and $L_i$, respectively.

The beam directing device 108A (FIG. 7A) utilizes a double pre-lens deflection using deflectors 116A and 118B accommodated in a spaced-apart relationship along the optical axis OA upstream of the objective lens plane 12. Optionally, additional in-lens and post-lens scanning deflectors 20 and 22 are provided to operate separately from the deflectors 116A and 118A, for example, to provide the tilt mode with the primary beam incidence onto the optical axis OA. In the present example, operation of these deflectors 20 and 22 is not illustrated. Thus, the primary electron beam $B_p$ propagating along the first axis OA' passes the primary beam hole 9A of the detector 9, and enters the deflection field of the deflector 116A that deflects the primary electron beam $B_p$ towards the optical axis OA. The primary electron beam is then deflected by the deflection field of the deflector 118A in the opposite direction to provide the beam propagation towards the wafer 2 along an axis OA" substantially coinciding with the optical axis OA. The primary electron beam $B_p$ thus impinges onto the location $L_1$ on the wafer, and knocks-out a secondary beam $B_s$ propagating back from the wafer along an axis parallel to the optical axis OA. The same deflection fields of the deflectors 118A and 116A sequentially affect the trajectory of the secondary beam $B_s$ providing its propagation along an axis OA''' to the region 9B of the detector.

The beam directing device 108B of FIG. 7B utilizes a double deflection formed by one pre-lens and one in-lens deflection—deflectors 116B and 118B. An additional post-lens deflector 22 may optionally be provided, for example, to operate together with the deflector 118B to provide the desired tilt mode. The primary and secondary beam propagation through the device 108B is shown in the figure in a self-explanatory manner. The detection of the secondary beam $B_s$ by the detector region 9B outside the primary beam hole 9A is provided.

FIG. 7C shows the beam directing device 108C, in which two deflectors—in lens deflector 116C and post-lens deflector 118C are used for affecting the trajectories of the primary and secondary beams. As indicated above, when using the focusing assembly of FIG. 1 (magnetic objective lens 12 and electrostatic lens 14), the pre-lens and in-lens deflectors are both accommodated within the focusing field of the entire focusing assembly. In FIG. 7C, the primary and secondary beams propagation scheme with the normal operational mode is shown in solid lines, and that of the tilt mode is shown in broken lines. Switching from the normal to tilt mode is achieved by appropriately varying the electrical parameters of the deflectors (increasing the electrical currents through the deflectors' coils). It should be understood that the tilt mode could similarly be obtained with the previously described examples as well.

Hence, in the above examples of FIGS. 7A–7C, similarly to the example of FIG. 4, the primary beam $B_p$ impinges onto the wafer 2 along the axis OA" parallel to the optical axis OA (in FIGS. 7A–7C substantially along the optical axis, and in FIG. 4—along an axis spaced-apart from the optical axis). The secondary electron beam $B_s$ is thereby always directed to the region 9b of the detector region outside the primary beam hole 9a.

Figure 8A:
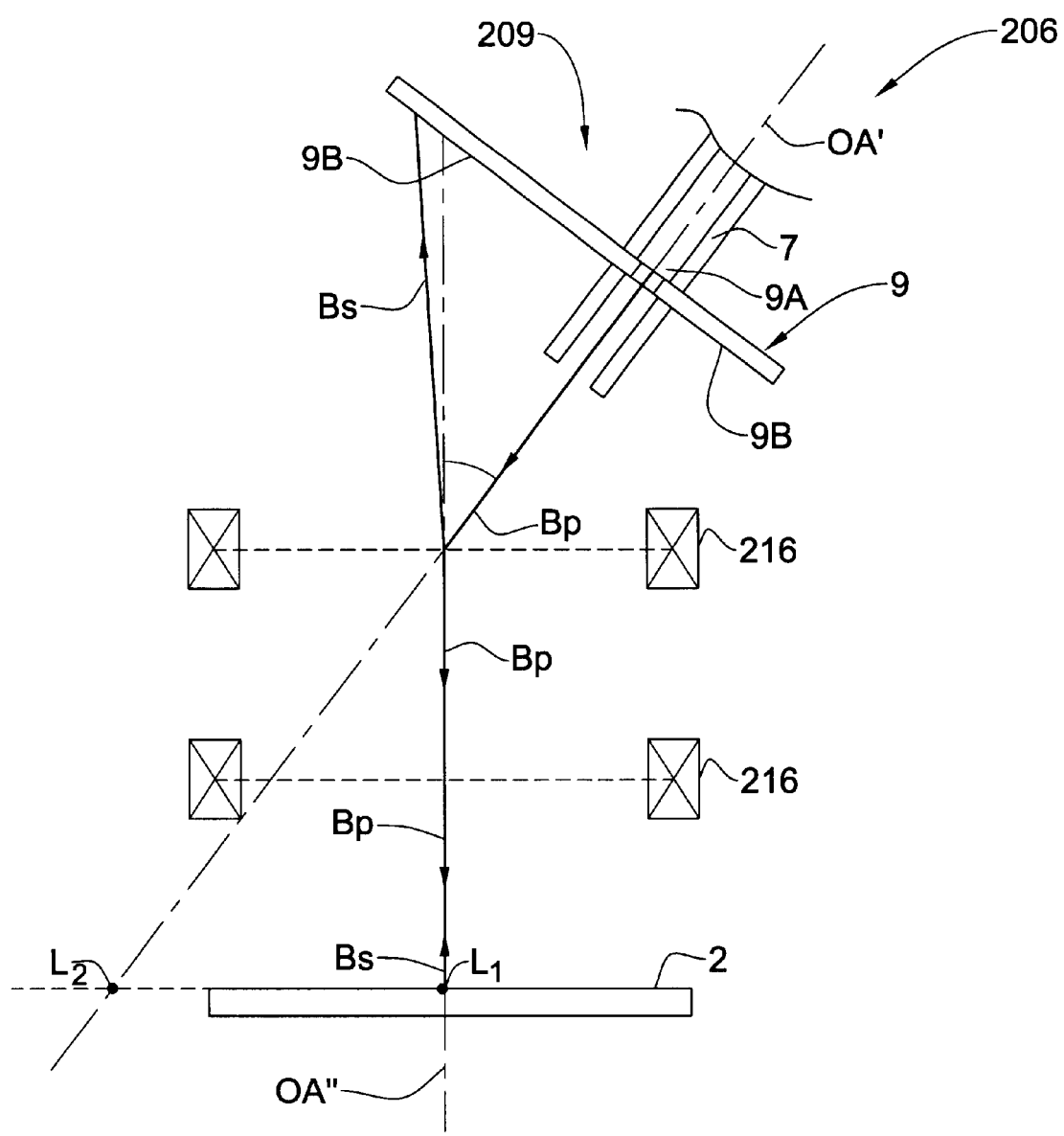
FIGS. 8A and 8B are schematic illustrations of a charged particle beam apparatus according to yet another embodiment of the invention, wherein FIG. 8A exemplifies the beams' propagation scheme with the normal mode, and FIG. 8B exemplifies the beams propagation scheme with the tilt mode.
Figure 8B:
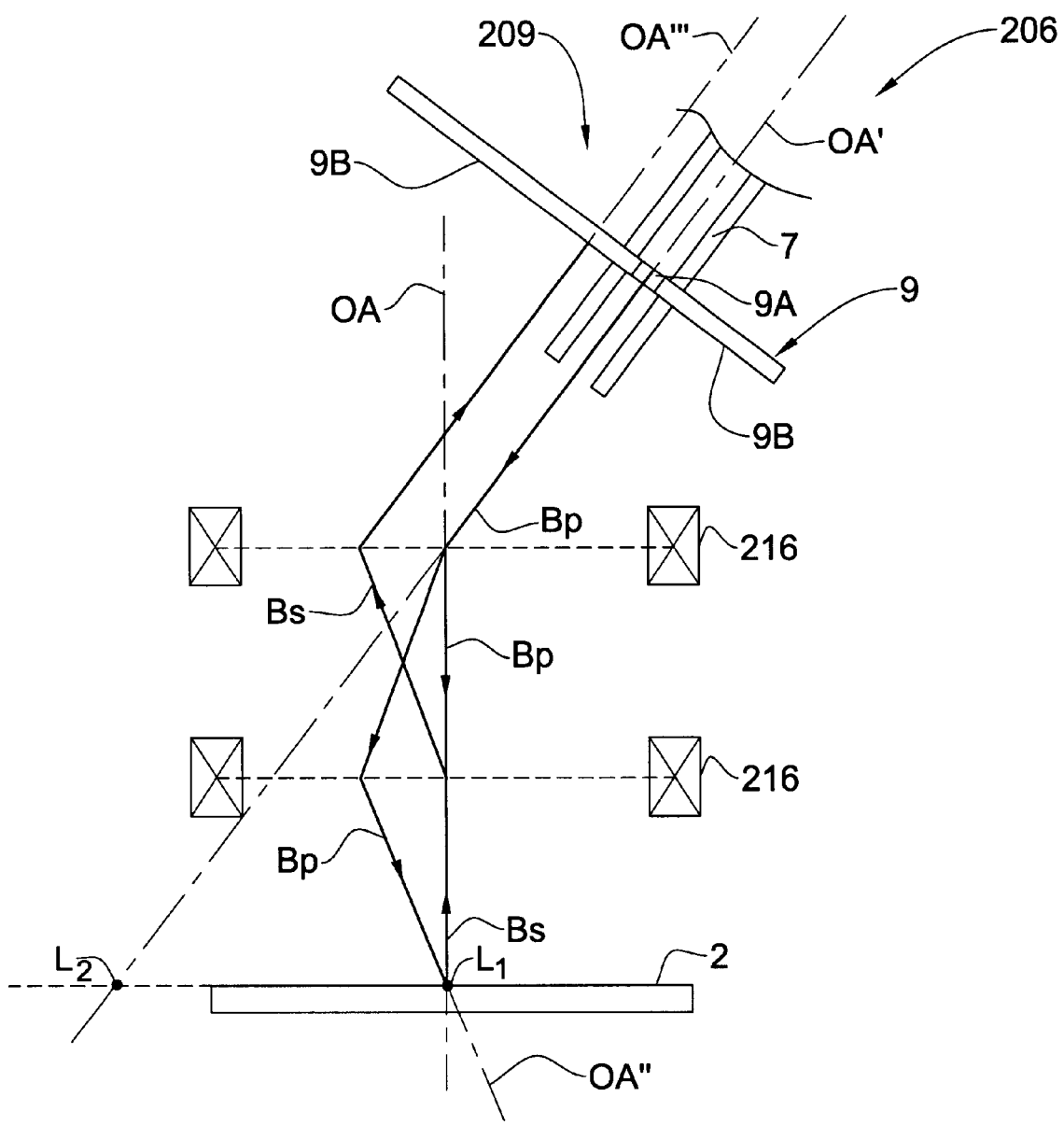

Referring to FIGS. 8A and 8B, there is illustrated a charged particle beam apparatus 206 according to yet another embodiment of the invention. Here, the anode tube (the first axis OA"), as well as the central axis of the detector 209, forms an angle with the optical axis OA of the focusing assembly of a beam directing device 208, for example, an angle of about 1–2°. Deflectors 216 and 218 of the beam directing device 208 may be two pre-lens deflectors, one pre-lens and one in-lens deflector, or one in-lens and one post-lens deflector. FIG. 8A exemplifies the beams' propagation scheme with the normal mode, and FIG. 8B exemplifies the beams propagation scheme with the tilt mode.

As shown in FIG. 8A, the primary beam $B_p$ propagates towards the beam directing device 208 along the first axis OA" passing through the primary beam hole 9B, and is deflected by the deflector 216 only to impinge onto the wafer 2 along a second axis $OA_1$" (substantially coinciding with the optical axis OA) forming an angle with the first axis OA'. The axis OA" intersects the wafer's surface at a location $L_1$ spaced-apart from a location $L_2$ of intersection between the first axis OA' and the wafer's surface. The secondary electron beam $B_s$ propagates back along the optical axis OA and is deflected by the same deflector 216 only to propagate to the region 9b of the detector outside the primary beam hole 9a.

As shown in FIG. 8B, the primary beam $B_p$ propagates along the first axis OA" passing through the primary beam hole 9A of the detector, and is then sequentially deflected by the deflectors 216 and 218 in opposite directions. This results in the primary beam incidence onto the location $L_1$ on the wafer along the second axis OA'. The secondary beam $B_s$ knocked-out from that location propagates back along the axis parallel to the optical axis OA, and is sequentially deflected by the deflectors 218 and 216, to thereby propagate along the OA''' to the detecting region 9B outside the primary beam hole.

It should be understood that, in the configuration of FIGS. 8A and 8B, the provision of a second deflector is optional for the purposes of the present invention, namely, for separating between the primary and secondary beams and directing the secondary beam to the detector region 9b when operating with the normal mode. However, in order to enable operation with the "tilt mode", the provision of at least two deflectors is preferred.

It should also be noted that a successful "side wall imaging" by tilting the incident beam can be achieved when no extraction electric field (or "boosting voltage") is used, namely when the following condition takes place: $V_{anode} \approx V_{pole/piece} \approx V_{wafer}$. In this case, although the provision of the second deflector may not sufficiently affect chromatic aberrations of deflection, the appropriate operation of this deflector would provide successful tilting of the incident beam, namely, which would enable the inspection of the same location on the wafer in the "normal" and "tilt" modes. The provision of the extraction field, however, typically improves imaging.

Those skilled in the art will readily appreciate that various modifications and changes may be applied to the embodiments of the invention as hereinbefore exemplified without departing from its scope as defined in and by the appended claims. The beam directing device and a the charged particle beam apparatus constructed and operated according to the invention may be used in any inspection, metrology, defect review or similar tool.

What is claimed is:

1. A method of separating between a primary charged particle beam and a secondary charged particle beam, the secondary charged particle beam resulting from interaction of the primary charged particle beam with a sample, the method comprising:
    (a) directing the primary charged particle beam along a first axis passing through an opening in a detector, which has charged particle detecting regions outside said opening; and
    (b) affecting the trajectory of the primary charged particle beam to provide the primary charged particle beam propagation to the sample along a second axis substantially parallel to and spaced-apart from said first axis, thereby causing the secondary charged particle beam propagation to the detecting region of said detector outside said opening.

2. The method according to claim 1, wherein said affecting comprises passing the primary charged particle beam through a deflection assembly producing two deflection fields, which deflect the primary charged particle beam from its propagation along the first axis to the propagation of the primary charged particle beam along the second axis, said two deflection fields deflecting the secondary charged particle to provide the propagation of the secondary charged particle beam to the detecting region of said detector outside said opening.

3. The method according to claim 1, wherein said affecting comprises passing the primary charged particle beam through a beam directing device including a focusing assembly having an optical axis parallel to said first axis, and a deflection assembly, the deflection assembly deflecting the primary charged particle beam to provide from its propagation along the first axis to the propagation of the primary charged particle beam along the second axis parallel to said optical axis of the focusing assembly.

4. The method according to claim 3, wherein said deflecting comprises applying to the primary charged particle beam two deflection fields at two successive locations along the optical axis of the focusing assembly.

5. The method according to claim 3, wherein said first axis is substantially parallel to and spaced-apart from the optical axis of the focusing assembly.

6. The method according to claim 5, wherein said second axis substantially coincides with the optical axis of the focusing assembly.

7. The method according to claim 3, wherein said first axis substantially coincides with the optical axis of the focusing assembly.

8. The method according to claim 7, wherein said second axis is parallel to and spaced-apart from the optical axis of the focusing assembly.

9. A method of separating between a primary charged particle beam and a secondary charged particle beam, the secondary charged particle beam resulting from interaction of the primary charged particle beam with the sample, the method comprising:

(a) directing the primary charged particle beam towards a deflection assembly along a first axis passing through an opening in a detector, which has charged particle detecting regions outside said opening;

(b) passing the primary charged particle beam through the deflection assembly thereby affecting the trajectory of the primary charged particle beam to provide the primary charged particle beam propagation to the sample along a second axis substantially parallel to and spaced-apart from said first axis, thereby causing the secondary charged particle beam propagation to the detecting region of said detector outside said opening.

10. A method of separating between a primary charged particle beam and a secondary charged particle beam, the secondary charged particle beam resulting from interaction of the primary charged particle beam with the sample, the method comprising:

(a) directing the primary charged particle beam towards a beam directing device along a first axis passing through an opening in a detector, which has charged particle detecting regions outside said opening;

(b) passing the primary charged particle beam through the beam directing device that includes a focusing assembly defining an optical axis and a deflection assembly, the deflection assembly being operable to produced two deflection fields in two successive regions, respectively, along the optical axis of the focusing assembly, to thereby affect the trajectory of the primary charged particle beam to provide the primary charged particle beam deflection from its propagation along the first axis to the propagation of the primary charged particle beam to the sample along a second axis substantially parallel to and spaced-apart from said first axis, said two deflection fields affecting the trajectory of the secondary charged particle beam to cause the secondary charged particle beam propagation to the detecting region of said detector outside said opening.

11. A method of separating between a primary charged particle beam and a secondary charged particle beam, the secondary charged particle beam resulting from interaction of the primary charged particle beam with the sample, the method comprising:

directing the primary charged particle beam towards a beam directing device along a first axis passing through an opening in a detector, which has charged particle detecting regions outside said opening;

passing the primary charged particle beam through the beam directing device that includes a focusing assembly defining an optical axis forming an angle with said first axis, and a deflection assembly, the deflection assembly being operable to deflect the primary charged particle beam from its propagation along the first axis to the propagation of the primary charged particle beam to the sample along a second axis substantially parallel to the optical axis of the focusing assembly, and to affect the trajectory of the secondary charged particle beam to provide the secondary charged particle beam propagation to the detecting region of said detector outside said opening.

12. A method of inspecting a sample with a charged particle beam, the method comprising the steps of:

providing a primary charged particle beam propagating towards a beam directing device along a first axis passing through an opening in a detector, which has charged particle detecting regions outside said opening;

passing the primary charged particle beam through the beam directing device that includes a focusing assembly defining an optical axis and a deflection assembly, to thereby affect the trajectory of said primary charged particle beam to cause the primary charged particle beam propagation along a second axis parallel to and spaced-apart from said first axis and to cause propagation of a secondary charged particle beam, produced by interaction between the primary charged particle beam and the sample, to the detecting region outside said opening.

13. The method according to claim 12, wherein first axis is substantially perpendicular to the sample's surface.

14. The method according to claim 13, wherein said first axis is substantially parallel to the optical axis of the focusing assembly.

15. The method according to claim 14, wherein said first axis substantially coincides with the optical axis of the focusing assembly, said second axis being parallel to and spaced-apart from the optical axis of the focusing assembly.

16. The method according to claim 13, wherein said first axis is spaced-apart from the optical axis of the focusing assembly.

17. The method according to claim 16, wherein said second axis substantially coincides with the optical axis of the focusing assembly.

18. The method according to claim 12, wherein the deflection assembly affects the trajectory of the primary charged particle beam by applying to the primary charged particle beam two deflection fields at successive locations along the optical axis of the focusing assembly, said deflection fields affecting the trajectory of the secondary charged particle beam to cause said propagation of the secondary charged particle beam to the detecting region outside said opening.

19. A method of inspecting a sample with a charged particle beam, the method comprising the steps of:

providing a primary charged particle beam propagating towards a beam directing device along a first axis passing through an opening in a detector, which has charged particle detecting regions outside said opening;

passing the primary charged particle beam through the beam directing device that includes a focusing assembly defining an optical axis forming an angle with said first axis, and a deflection assembly, to thereby affect the trajectory of said primary charged particle beam to cause the primary charged particle beam propagation along a second axis parallel to and spaced-apart from said first axis and to cause propagation of a secondary charged particle beam, produced by interaction between the primary charged particle beam and the sample, to the detecting region outside said opening.

20. The method according to claim 19, wherein the deflection assembly affects the trajectory of the primary charged particle beam by applying thereto at least one deflection field that deflects the primary charged particle beam from its propagation along the first axis to the propagation of the primary charged particle beam along the second axis substantially parallel to the optical axis of the focusing assembly, said at least one deflection field deflecting the secondary charged particle beam to cause said propagation of the secondary charged particle beam to the detecting region outside said opening.

21. A beam directing device for use in a charged particle beam apparatus, which defines a primary charged particle beam propagating towards the beam directing device along a first axis and utilizes a detector that is formed with an opening and charged particle detecting regions outside said opening and is accommodated such that said first axis passes through said opening of the detector, the beam directing device comprising:

a focusing assembly that defines an optical axis and is operable to focus the primary charged particle beam onto a sample; and a deflection assembly operable to affect the trajectory of the primary charged particle beam to direct the primary charged particle beam onto the sample along a second axis substantially parallel to and spaced-apart from said first axis, thereby causing the secondary charged particle beam propagation to the detecting region of said detector outside said opening.

22. The device according to claim 21, wherein said optical axis is substantially parallel to said first axis of the primary charged particle beam propagation.

23. The device according to claim 22, wherein said optical axis substantially coincides with said first axis, said second axis being spaced-apart from said optical axis.

24. The device according to claim 21, wherein said optical axis is spaced-apart from said first axis.

25. The device according to claim 24, wherein said second axis substantially coincides with the optical axis of the focusing assembly.

26. The device according to claim 21, wherein said deflection assembly comprises two deflectors accommodated at two spaced-apart locations along the optical axis of the focusing assembly and operable to apply two deflection fields to the primary charged particle beam and to the secondary charged particle beam.

27. The device according to claim 21, wherein said focusing assembly comprises a magnetic objective lens.

28. The device according to claim 27, wherein said focusing assembly further comprises an electrostatic immersion lens accommodated downstream of the magnetic objective lens with respect to the direction of the primary beam propagation to the sample.

29. The device according to claim 27, wherein said deflection assembly comprises two deflectors accommodated at two spaced-apart locations along the optical axis of the focusing assembly and operable to apply two deflection fields to the primary charged particle beam and to the secondary charged particle beam.

30. The device according to claim 29, wherein one deflector is located upstream of the magnetic objective lens, and the other deflector is located downstream of the magnetic objective lens, with respect to the direction of the primary beam propagation to the sample.

31. The device according to claim 29, wherein the deflectors are located upstream of the magnetic objective lens with respect to the direction of the primary beam propagation to the sample.

32. The device according to claim 29, wherein one deflector is located upstream of the magnetic objective lens with respect to the direction of the primary beam propagation to the sample, and the other deflector is located adjacent to the magnetic objective lens.

33. The device according to claim 29, wherein one deflector is located downstream of the magnetic objective lens with respect to the direction of the primary beam propagation to the sample, and the other deflector is located adjacent to the magnetic objective lens.

34. A beam directing device for use in a charged particle beam apparatus, which defines a primary charged particle beam propagating towards the beam directing device along a first axis and utilizes a detector that is formed with an opening and charged particle detecting regions outside said opening and is accommodated such that said first axis passes through said opening of the detector, the beam directing device comprising:

a focusing assembly that defines an optical axis that forms an angle with said first axis and is operable to focus the primary charged particle beam onto a sample; and a deflection assembly operable to affect the trajectory of the primary charged particle beam to direct the primary charged particle beam onto the sample along a second axis substantially parallel to the first axis, thereby causing the secondary charged particle beam propagation to the detecting region of said detector outside said opening.

35. A charged particle beam apparatus for inspecting a sample comprising:

an anode tube defining a space of propagation of a primary beam of charged particles generated by a particles' source along a first axis substantially parallel to a longitudinal axis of the anode tube;

a detector formed with an opening and having charged particle detecting regions outside said opening, the detector being accommodated such that said first axis intersects with said opening; and a beam directing device accommodated in the path of the primary charged particle beam passed through said opening in the detector, the beam directing device comprising a focusing assembly, which defines an optical axis and is operable to focus the primary charged particle beam onto the sample, and a deflection assembly, which is operable to affect the trajectory of the primary charged particle beam to cause the primary charged particle beam propagation to the sample along a second axis substantially-parallel to and spaced-apart from said first axis, and to affect the trajectory of the secondary charged particle beam, thereby providing the secondary charged particle beam propagation to the region of said detector outside said opening.

36. The apparatus according to claim 35, wherein said first axis is substantially parallel to the optical axis of the focusing assembly.

37. The apparatus according to claim 36, wherein said optical axis substantially coincides with said first axis, said second axis being spaced-apart from said optical axis.

38. The apparatus according to claim 35, wherein said optical axis is spaced-apart from said first axis.

39. The apparatus according to claim 38, wherein said second axis substantially coincides with the optical axis of the focusing assembly.

40. The apparatus according to claim 35, wherein said deflection assembly comprises two deflectors accommodated at two spaced-apart locations along the optical axis of the focusing assembly and operable to apply two deflection fields to the primary charged particle beam and to the secondary charged particle beam.

41. The apparatus according to claim 35, wherein said focusing assembly comprises a magnetic objective lens.

42. The apparatus according to claim 41, wherein said focusing assembly further comprises an electrostatic immersion lens accommodated downstream of the magnetic objective lens with respect to the direction of the primary beam propagation to the sample.

43. A charged particle beam apparatus for inspecting a sample comprising:

an anode tube defining a space of propagation of a primary beam of charged particles generated by a particles' source along a first axis substantially parallel to a longitudinal axis of the anode tube;

a detector formed with an opening and having charged particle detecting regions outside said opening, the detector being accommodated such that said first axis intersects with said opening; and a beam directing device accommodated in the path of the primary charged particle beam passed through said opening in the detector, the beam directing device comprising a focusing assembly, which defines an optical axis forming an angle with said first axis and is operable to focus the primary charged particle beam onto the sample, and a deflection assembly, which is operable to affect the trajectory of the primary charged particle beam to cause the primary charged particle beam propagation to the sample along a second axis substantially parallel to the optical axis of the focusing assembly, and to affect the trajectory of the secondary charged particle beam, thereby providing the secondary charged particle beam propagation to the region of said detector outside said opening.

* * * * *

(12) EX PARTE REEXAMINATION CERTIFICATE (5939th)
United States Patent
Petrov et al.

(10) Number: US 6,674,075 C1
(45) Certificate Issued: Oct. 9, 2007

(54) CHARGED PARTICLE BEAM APPARATUS AND METHOD FOR INSPECTING SAMPLES

(75) Inventors: Igor Petrov, Holon (IL); Zvika Rosenberg, Jerusalem (IL)

(73) Assignee: Applied Materials, Israel Ltd., Rehovot, IL (US)

Reexamination Request:
No. 90/007,037, May 10, 2004

Reexamination Certificate for:
Patent No.: 6,674,075
Issued: Jan. 6, 2004
Appl. No.: 10/146,218
Filed: May 13, 2002

(51) Int. Cl.
*H01J 37/26* (2006.01)
*G21K 1/08* (2006.01)

(52) U.S. Cl. .................. 250/310; 250/307; 250/311; 250/396 R; 250/396 ML; 250/492.1
(58) Field of Classification Search ............... None
See application file for complete search history.

(56) References Cited

U.S. PATENT DOCUMENTS

| | | |
|---|---|---|
| 4,896,036 A | 1/1990 | Rose et al. |
| 6,184,526 B1 | 2/2001 | Kohama et al. |
| 6,194,729 B1 | 2/2001 | Weimer |

FOREIGN PATENT DOCUMENTS

| | | |
|---|---|---|
| WO | WO 99/46797 | 9/1999 |
| WO | WO 01/45136 | 6/2001 |
| WO | WO 02/37523 | 5/2002 |

OTHER PUBLICATIONS

International Search Report, PCT/US03/15018, May 12, 2003.
Patent Abstract of Japan.
Patent Abstract of Japan, vol. 014, No. 385 (P–1094), Aug. 20, 1990, & JP 02 145947 A (Shimadzu Corp.), Jun. 5, 1990, abstract; figure 1.

*Primary Examiner*—Minh Nguyen

(57) ABSTRACT

A beam directing method and device are presented for spatially separating between a primary charged particle beam and a beam of secondary particles returned from a sample as a result of its interaction with the primary charged particle beam. The primary charged particle beam is directed towards the beam directing device along a first axis passing an opening in a detector, which has charged particle detecting regions outside this opening. The trajectory of the primary charged particle beam is then affected to cause the primary charged particle beam propagation to the sample along a second axis substantially parallel to and spaced-apart from the first axis. This causes the secondary charged particle beam propagation to the detecting region outside the opening in the detector.

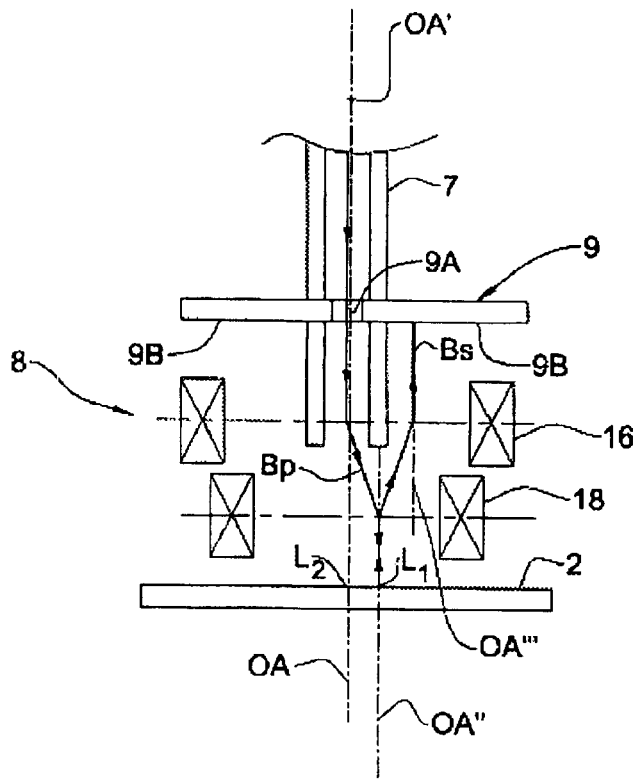

US 6,674,075 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4, 9–10, 12–17 and 19–20, 26–27, 29–33, 40–41 are cancelled.

Claims 1–3, 11, 18, 21 and 28, 34–35, 42–43 are determined to be patentable as amended.

Claims 5–8, 22–25 and 36–39, dependent on an amended claim, are determined to be patentable.

New claims 44–79 are added and determined to be patentable.

1. A method [of separating between a primary charged particle beam and a secondary charged particle beam, the secondary charged particle beam resulting from interaction of the primary charged particle beam with a sample, the method] comprising:
  (a) directing [the] *a* primary charged particle beam along a first axis passing through an opening in a detector, which has charged particle detecting regions outside said opening; and
  (b) affecting, [the] *by passing the primary charged particle beam through a deflection assembly having a magnetic objective lens focusing assembly and deflectors operable to apply deflection fields to the primary charged particle beam at spaced-apart locations along an optical axis of the focusing assembly, at least one of which is located upstream of the magnetic objective lens and another of which is located downstream of the magnetic objective lens, each with respect to the direction of the primary beam propagation, a* trajectory of the primary charged particle beam [to provide the primary charged particle beam] *from its* propagation along the first axis to [the] *propagation towards a* sample *and* along a second axis substantially parallel to and spaced-apart from said first axis, thereby causing [the] *a* secondary charged particle beam [propagation] *resulting from interaction of the primary charged particle beam with the sample to propagate* to the detecting [region] *regions* of said detector outside said opening.

2. The method according to claim 1, wherein said affecting comprises passing the primary charged particle beam through [a deflection assembly producing] two deflection fields, which deflect the primary charged particle beam from its propagation along the first axis to the propagation of the primary charged particle beam along the second axis, said two deflection fields deflecting the secondary charged particle to provide the propagation of the secondary charged particle beam to the detecting [region] *regions* of said detector outside said opening.

3. The method according to claim 1, wherein [said affecting comprises passing the primary charged particle beam through a beam directing device including a focusing assembly having an] *the* optical axis *of the focusing assembly is* parallel to said first axis[, and a deflection assembly, the deflection assembly deflecting the primary charged particle beam to provide from its propagation along the first axis to the propagation of the primary charged particle beam along the second axis parallel to said optical axis of the focusing assembly].

11. A method [of separating between a primary charged particle beam and a secondary charged particle beam, the secondary charged particle beam resulting from interaction of the primary charged particle beam with the sample, the method] comprising:
  directing [the] *a* primary charged particle beam towards a beam directing device along a first axis passing through an opening in a detector, which has charged particle detecting regions outside said opening;
  passing the primary charged particle beam through the beam directing device that includes: (*a*) *a focusing assembly, and* (*b*) *a deflection assembly, the focusing assembly* defining an optical axis [forming an] *having a non-zero* angle with said first axis, and [a deflection assembly,] the deflection assembly being operable to:
  (*i*) deflect the primary charged particle beam from its propagation along the first axis to [the] propagation of the primary charged particle beam [to the] *towards a* sample along a second axis substantially parallel to the optical axis of the focusing assembly, and [to] (*ii*) affect [the] *a* trajectory of [the] *a* secondary charged particle beam *resulting from interaction of the primary charged particle beam with the sample* to provide the secondary charged particle beam propagation to the detecting [region] *regions* of said detector outside said opening.

18. The method according to claim [12] *11*, wherein the deflection assembly [affects] *is operable to deflect* [the trajectory of] the primary charged particle beam by applying to the primary charged particle beam two deflection fields at successive locations along the optical axis of the focusing assembly, said deflection fields affecting the trajectory of the secondary charged particle beam to cause said propagation of the secondary charged particle beam to the detecting [region] *regions of said detector* outside said opening.

21. A beam directing device for use in a charged particle beam apparatus, which defines a primary charged particle beam propagating towards the beam directing device along a first axis and utilizes a detector that is formed with an opening and charged particle detecting regions outside said opening and is accommodated such that said first axis passes through said opening of the detector, the beam directing device comprising:
  a focusing assembly that defines an optical axis and is operable to focus the primary charged particle beam onto a sample *at least in part using a magnetic objective lens;* and
  a deflection assembly (*i*) *having two deflectors accommodated at two spaced-apart locations along the optical axis of the focusing assembly, one of which is located upstream of the magnetic objective lens and another of which is located downstream of the magnetic objective lens, each with respect to the direction of the primary beam propagation to the sample, and* (*ii*) operable to affect [the] *a* trajectory of the primary charged particle beam to direct the primary charged particle beam onto the sample along a second axis substantially parallel to and spaced-apart from said first axis, thereby causing the secondary charged particle beam propagation to the detecting [region] *regions* of said detector outside said opening *by applying two deflection fields to the primary charged particle beam and to the secondary charged particle beam.*

28. The device according to claim [27] *21*, wherein said focusing assembly further comprises an electrostatic immersion lens accommodated downstream of the magnetic objective lens with respect to the direction of the primary beam propagation to the sample.

34. A beam directing device for use in a charged particle beam apparatus, which defines a primary charged particle beam propagating towards the beam directing device along a first axis and utilizes a detector that is formed with an opening and charged particle detecting regions outside said opening and is accommodated such that said first axis passes through said opening of the detector, the beam directing device comprising:

a focusing assembly that defines an optical axis [that forms an] *having a non-zero* angle with said first axis and is operable to focus the primary charged particle beam onto a sample; and a deflection assembly operable to affect the trajectory of the primary charged particle beam to direct the primary charged particle beam onto the sample along a second axis substantially parallel to the [first] *optical* axis [, thereby causing the] *of the focusing assembly and to direct propagation of a* secondary charged particle beam [propagation] *resulting from interaction of the primary charged particle beam with the sample* to the detecting [region] *regions* of said detector outside said opening.

35. A charged particle beam apparatus for inspecting a sample comprising:

an anode tube defining a space of propagation of a primary beam of charged particles generated by a [particles'] *particle* source along a first axis substantially parallel to a longitudinal axis of the anode tube;

a detector formed with an opening and having charged particle detecting regions outside said opening, the detector being accommodated such that said first axis intersects with said opening; and a beam directing device accommodated in the path of the primary charged particle beam passed through said opening in the detector, the beam directing device comprising a focusing assembly, which defines an optical axis and is operable to focus the primary charged particle beam onto the sample *at least in part using a magnetic objective lens*, and a deflection assembly *(i) having two deflectors accommodated at two spaced-apart locations along the optical axis of the focusing assembly, one of which is located upstream of the magnetic objective lens and another of which is located downstream of the magnetic objective lens, each with respect to the direction of the primary beam propagation to the sample, and (ii)* which is operable to affect [the] *a* trajectory of the primary charged particle beam to cause the primary charged particle beam propagation to the sample along a second axis substantially-parallel to and spaced-apart from said first axis, and to affect [the] *a* trajectory of [the] *a* secondary charged particle beam *resulting from interaction of the primary charged particle beam with the sample*, thereby providing the secondary charged particle beam propagation to the [region] *regions* of said detector outside said opening by applying two deflection fields to the primary charged particle beam *and to the secondary charged particle beam.*

42. The apparatus according to claim [41] *35*, wherein said focusing assembly further comprises an electrostatic immersion lens accommodated downstream of the magnetic objective lens with respect to the direction of the primary beam propagation to the sample.

43. A charged particle beam apparatus for inspecting a sample comprising:

an anode tube defining a space of propagation of a primary beam of charged particles generated by a [particles'] *particle* source along a first axis substantially parallel to a longitudinal axis of the anode tube;

a detector formed with an opening and having charged particle detecting regions outside said opening, the detector being accommodated such that said first axis intersects with said opening; and a beam directing device accommodated in the path of the primary charged particle beam passed through said opening in the detector, the beam directing device comprising a focusing assembly, which defines an optical axis [forming an] *having a non-zero* angle with said first axis and is operable to focus the primary charged particle beam onto the sample, and a deflection assembly, which is operable to affect [the] *a* trajectory of the primary charged particle beam to cause the primary charged particle beam propagation to the sample along a second axis substantially parallel to the optical axis of the focusing assembly, and to affect [the] *a* trajectory of [the] *a* secondary charged particle beam *resulting from interaction of the primary charged particle beam with the sample*, thereby providing the secondary charged particle beam propagation to the [region] *regions* of said detector outside said opening.

*44. A method comprising:*

*(a) directing a primary charged particle beam along a first axis passing through an opening in a detector, which has charged particle detecting regions outside said opening; and*

*(b) affecting, by passing the primary charged particle beam through a deflection assembly having a magnetic objective lens focusing assembly and deflectors operable to apply deflection fields to the primary charged particle beam at spaced-apart locations along an optical axis of the focusing assembly, at least one of which is located upstream of the magnetic objective lens with respect to the direction of the primary beam propagation and another of which is located adjacent to the magnetic objective lens, a trajectory of the primary charged particle beam from its propagation along the first axis to propagation towards a sample and along a second axis substantially parallel to and spaced-apart from said first axis, thereby causing a secondary charged particle beam resulting from interaction of the primary charged particle beam with the sample to propagate to the detecting regions of said detector outside said opening.*

*45. The method according to claim 44, wherein said affecting comprises passing the primary charged particle beam through two deflection fields, which deflect the primary charged particle beam from its propagation along the first axis to the propagation of the primary charged particle beam along the second axis, said two deflection fields deflecting the secondary charged particle to provide the propagation of the secondary charged particle beam to the detecting regions of said detector outside said opening.*

*46. The method according to claim 44, wherein the optical axis of the focusing assembly is parallel to said first axis.*

47. The method according to claim 46, wherein said first axis is substantially parallel to and spaced-apart from the optical axis of the focusing assembly.

48. The method according to claim 47, wherein said second axis substantially coincides with the optical axis of the focusing assembly.

49. The method according to claim 46, wherein said first axis substantially coincides with the optical axis of the focusing assembly.

50. The method according to claim 49, wherein said second axis is parallel to and spaced-apart from the optical axis of the focusing assembly.

51. A method comprising:
(a) directing a primary charged particle beam along a first axis passing through an opening in a detector, which has charged particle detecting regions outside said opening; and
(b) affecting, by passing the primary charged particle beam through a deflection assembly having a magnetic objective lens focusing assembly and deflectors operable to apply deflection fields to the primary charged particle beam at spaced-apart locations along an optical axis of the focusing assembly, at least one of which is located downstream of the magnetic objective lens with respect to the direction of the primary beam propagation and another of which is located adjacent to the magnetic objective lens, a trajectory of the primary charged particle beam from its propagation along the first axis to propagation towards a sample and along a second axis substantially parallel to and spaced-apart from said first axis, thereby causing a secondary charged particle beam resulting from interaction of the primary charged particle beam with the sample to propagate to the detecting regions of said detector outside said opening.

52. The method according to claim 51, wherein said affecting comprises passing the primary charged particle beam through two deflection fields, which deflect the primary charged particle beam from its propagation along the first axis to the propagation of the primary charged particle beam along the second axis, said two deflection fields deflecting the secondary charged particle to provide the propagation of the secondary charged particle beam to the detecting regions of said detector outside said opening.

53. The method according to claim 51, wherein the optical axis of the focusing assembly is parallel to said first axis.

54. The method according to claim 53, wherein said first axis is substantially parallel to and spaced-apart from the optical axis of the focusing assembly.

55. The method according to claim 54, wherein said second axis substantially coincides with the optical axis of the focusing assembly.

56. The method according to claim 53, wherein said first axis substantially coincides with the optical axis of the focusing assembly.

57. The method according to claim 56, wherein said second axis is parallel to and spaced-apart from the optical axis of the focusing assembly.

58. A beam directing device for use in a charged particle beam apparatus, which defines a primary charged particle beam propagating towards the beam directing device along a first axis and utilizes a detector that is formed with an opening and charged particle detecting regions outside said opening and is accommodated such that said first axis passes through said opening of the detector, the beam directing device comprising:
a focusing assembly that defines an optical axis and is operable to focus the primary charged particle beam onto a sample at least in part using a magnetic objective lens; and
a deflection assembly (i) having two deflectors accommodated at two spaced-apart locations along the optical axis of the focusing assembly, one of which is located upstream of the magnetic objective lens with respect to the direction of the primary beam propagation to the sample and another of which is located adjacent to the magnetic objective lens, and (ii) operable to affect a trajectory of the primary charged particle beam to direct the primary charged particle beam onto the sample along a second axis substantially parallel to and spaced-apart from said first axis, thereby causing a secondary charged particle beam propagation to the detecting regions of said detector outside said opening by applying two deflection fields to the primary charged particle beam and to the secondary charged particle beam.

59. The device according to claim 58, wherein said optical axis is substantially parallel to said first axis of the primary charged particle beam propagation.

60. The device according to claim 59, wherein said optical axis substantially coincides with said first axis, said second axis being spaced-apart from said optical axis.

61. The device according to claim 58, wherein said optical axis is spaced-apart from said first axis.

62. The device according to claim 61, wherein said second axis substantially coincides with the optical axis of the focusing assembly.

63. The device according to claim 58, wherein said focusing assembly further comprises an electrostatic immersion lens accommodated downstream of the magnetic objective lens with respect to the direction of the primary beam propagation to the sample.

64. A beam directing device for use in a charged particle beam apparatus, which defines a primary charged particle beam propagating towards the beam directing device along a first axis and utilizes a detector that is formed with an opening and charged particle detecting regions outside said opening and is accommodated such that said first axis passes through said opening of the detector, the beam directing device comprising:
a focusing assembly that defines an optical axis and is operable to focus the primary charged particle beam onto a sample at least in part using a magnetic objective lens; and
a deflection assembly (i) having two deflectors accommodated at two spaced-apart locations along the optical axis of the focusing assembly, one of which is located downstream of the magnetic objective lens with respect to the direction of the primary beam propagation to the sample and another of which is located adjacent to the magnetic lens, and (ii) operable to affect a trajectory of the primary charged particle beam to direct the primary charged particle beam onto the sample along a second axis substantially parallel to and spaced-apart from said first axis, thereby causing a secondary charged particle beam propagation to the detecting regions of said detector outside said opening by applying two deflection fields to the primary charged particle beam and to the secondary charged particle beam.

65. The device according to claim 64, wherein said optical axis is substantially parallel to said first axis of the primary charged particle beam propagation.

66. The device according to claim 65, wherein said optical axis substantially coincides with said first axis, said second axis being spaced-apart from said optical axis.

67. The device according to claim 64, wherein said optical axis is spaced-apart from said first axis.

68. The device according to claim 67, wherein said second axis substantially coincides with the optical axis of the focusing assembly.

69. The device according to claim 64, wherein said focusing assembly further comprises an electrostatic immersion lens accommodated downstream of the magnetic objective lens with respect to the direction of the primary beam propagation to the sample.

70. A charged particle beam apparatus for inspecting a sample comprising:

an anode tube defining a space of propagation of a primary beam of charged particles generated by a particle source along a first axis substantially parallel to a longitudinal axis of the anode tube;

a detector formed with an opening and having charged particle detecting regions outside said opening, the detector being accommodated such that said first axis intersects with said opening; and a beam directing device accommodated in the path of the primary charged particle beam passed through said opening in the detector, the beam directing device comprising a focusing assembly, which defines an optical axis and is operable to focus the primary charged particle beam onto the sample at least in part using a magnetic objective lens, and a deflection assembly (i) having two deflectors accommodated at two spaced-apart locations along the optical axis of the focusing assembly, one of which is located upstream of the magnetic objective lens with respect to the direction of the primary beam propagation to the sample and another of which is located adjacent to the magnetic objective lens, and (ii) operable to affect a trajectory of the primary charged particle beam to cause the primary charged particle beam propagation to the sample along a second axis substantially-parallel to and spaced-apart from said first axis, and to affect a trajectory of a secondary charged particle beam resulting from interaction of the primary charged particle beam with the sample, thereby providing the secondary charged particle beam propagation to the regions of said detector outside said opening by applying two deflection fields to the primary charged particle beam and to the secondary charged particle beam.

71. The apparatus according to claim 70, wherein said first axis is substantially parallel to the optical axis of the focusing assembly.

72. The apparatus according to claim 71, wherein said optical axis substantially coincides with said first axis, said second axis being spaced-apart from said optical axis.

73. The apparatus according to claim 70, wherein said optical axis is spaced-apart from said first axis.

74. The apparatus according to claim 73, wherein said second axis substantially coincides with the optical axis of the focusing assembly.

75. A charged particle beam apparatus for inspecting a sample comprising:

an anode tube defining a space of propagation of a primary beam of charged particles generated by a particle source along a first axis substantially parallel to a longitudinal axis of the anode tube;

a detector formed with an opening and having charged particle detecting regions outside said opening, the detector being accommodated such that said first axis intersects with said opening; and a beam directing device accommodated in the path of the primary charged particle beam passed through said opening in the detector, the beam directing device comprising a focusing assembly, which defines an optical axis and is operable to focus the primary charged particle beam onto the sample at least in part using a magnetic objective lens, and a deflection assembly (i) having two deflectors accommodated at two spaced-apart locations along the optical axis of the focusing assembly, one of which is located downstream of the magnetic objective lens with respect to the direction of the primary beam propagation to the sample and another of which is located adjacent to the magnetic objective lens, and (ii) operable to affect a trajectory of the primary charged particle beam to cause the primary charged particle beam propagation to the sample along a second axis substantially-parallel to and spaced-apart from said first axis, and to affect a trajectory of a secondary charged particle beam resulting from interaction of the primary charged particle beam with the sample, thereby providing the secondary charged particle beam propagation to the regions of said detector outside said opening by applying two deflection fields to the primary charged particle beam and to the secondary charged particle beam.

76. The apparatus according to claim 75, wherein said first axis is substantially parallel to the optical axis of the focusing assembly.

77. The apparatus according to claim 76, wherein said optical axis substantially coincides with said first axis, said second axis being spaced-apart from said optical axis.

78. The apparatus according to claim 75, wherein said optical axis is spaced-apart from said first axis.

79. The apparatus according to claim 78, wherein said second axis substantially coincides with the optical axis of the focusing assembly.

* * * * *